United States Patent
Kaviratna et al.

(10) Patent No.: US 10,676,619 B2
(45) Date of Patent: Jun. 9, 2020

(54) PIGMENT POWDERS

(71) Applicant: Merck Patent GmbH, Darmstadt (DE)

(72) Inventors: Padma Kaviratna, Pooler, GA (US);
Mark Tellefsen, Savannah, GA (US);
Qingmin Cheng, Rincon, GA (US);
Matthew Eddens, Pooler, GA (US);
Qinyun Peng, Columbus, NJ (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/924,527

(22) Filed: Mar. 19, 2018

(65) Prior Publication Data

US 2018/0265708 A1    Sep. 20, 2018

Related U.S. Application Data

(60) Provisional application No. 62/473,581, filed on Mar. 20, 2017.

(51) Int. Cl.
| | |
|---|---|
| *C09C 1/00* | (2006.01) |
| *C09D 7/62* | (2018.01) |
| *C09C 3/00* | (2006.01) |
| *A61K 8/20* | (2006.01) |
| *A61K 8/02* | (2006.01) |
| *A61Q 1/10* | (2006.01) |
| *A61Q 1/06* | (2006.01) |
| *A61Q 5/02* | (2006.01) |
| *A61Q 3/02* | (2006.01) |
| *A61K 8/25* | (2006.01) |
| *A61K 8/19* | (2006.01) |
| *A61Q 1/02* | (2006.01) |
| *A61Q 19/00* | (2006.01) |

(52) U.S. Cl.
CPC .......... *C09C 1/0045* (2013.01); *A61K 8/022* (2013.01); *A61K 8/0254* (2013.01); *A61K 8/19* (2013.01); *A61K 8/20* (2013.01); *A61K 8/25* (2013.01); *A61Q 1/02* (2013.01); *A61Q 1/06* (2013.01); *A61Q 1/10* (2013.01); *A61Q 3/02* (2013.01); *A61Q 5/02* (2013.01); *A61Q 19/00* (2013.01); *C09C 1/0015* (2013.01); *C09C 1/0021* (2013.01); *C09C 3/00* (2013.01); *C09D 7/62* (2018.01); *A61K 2800/43* (2013.01); *A61K 2800/436* (2013.01); *A61K 2800/621* (2013.01); *A61K 2800/622* (2013.01); *A61K 2800/651* (2013.01); *C09C 1/0024* (2013.01); *C09C 1/0036* (2013.01); *C09C 1/0051* (2013.01); *C09C 1/0063* (2013.01); *C09C 2200/1087* (2013.01); *C09C 2200/301* (2013.01); *C09C 2220/10* (2013.01); *C09C 2220/103* (2013.01)

(58) Field of Classification Search
CPC ... C09C 1/0045; C09C 1/0015; C09C 1/0021; C09C 1/0024; C09C 1/0036; C09C 1/0051; C09C 1/0063; C09C 2200/1087; C09C 2200/301; C09C 2220/10; C09C 2220/103; C09D 7/62; A61K 8/022; A61K 8/0254; A61K 8/19; A61K 8/20; A61K 8/25; A61K 2800/43; A61K 2800/436; A61K 2800/621; A61Q 1/02; A61Q 1/06; A61Q 1/10; A61Q 3/02; A61Q 5/02; A61Q 9/00

See application file for complete search history.

(56) References Cited

U.S. PATENT DOCUMENTS

| | | | |
|---|---|---|---|
| 5,496,565 A | 3/1996 | Heinze et al. | |
| 6,579,357 B1 | 6/2003 | Cao | |
| 6,596,070 B1* | 7/2003 | Schmidt | A61Q 1/02 106/415 |
| 6,743,285 B1 | 6/2004 | Anselmann et al. | |
| 7,318,862 B2 | 1/2008 | Carsten et al. | |
| 2005/0252417 A1 | 11/2005 | Carsten et al. | |
| 2008/0110371 A1 | 5/2008 | Hollman et al. | |
| 2008/0279796 A1 | 11/2008 | Handrosch et al. | |
| 2012/0219607 A1* | 8/2012 | Schmidt | A61K 8/29 424/401 |

(Continued)

FOREIGN PATENT DOCUMENTS

| | | |
|---|---|---|
| DE | 1003377 B | 2/1957 |
| DE | 4305280 A1 | 8/1994 |
| DE | 102007010986 A1 | 9/2008 |
| EP | 2584010 B1 | 12/2013 |

(Continued)

OTHER PUBLICATIONS

Search report in corresponding EP3376900A1 dated Apr. 26, 2018 (pp. 1-2).
Machine translation of DE4305280.
Machine translation of bibliographic abstract for DE1003377.

*Primary Examiner* — Pegah Parvini

(74) *Attorney, Agent, or Firm* — Millen White Zelano and Branigan, PC; Csaba Henter

(57) ABSTRACT

Disclosed are pigment powders containing only coated BiOCl flakes, which flakes area) BiOCl flakes having a coating containing yellow iron oxide $Fe_2O_3 \cdot xH_2O$, optionally a colorant, optionally an adjuvant, and optionally $SiO_2$, b) BiOCl flakes having a coating containing $SiO_2$, optionally a colorant, and optionally an adjuvant, c) BiOCl flakes having a coating containing a colorant, $SiO_2$, optionally yellow iron oxide $Fe_2O_3 \cdot xH_2O$, and optionally an adjuvant, or d) BiOCl flakes having a coating containing $Fe_3O_4$ and optionally $SiO_2$, to a process for the preparation of the pigment powders, and to the use thereof especially in cosmetic formulations.

19 Claims, No Drawings

(56) References Cited

U.S. PATENT DOCUMENTS

2016/0145438 A1\* 5/2016 Ponce ..................... B05D 1/18
424/401

FOREIGN PATENT DOCUMENTS

| JP | 2001279126 A | 10/2001 |
|----|--------------|---------|
| JP | 2012180403 A | 9/2012  |

\* cited by examiner

PIGMENT POWDERS

The present invention relates to pigment powders consisting of coated BiOCl flakes, to a process for the preparation of the pigment powders, and to the use thereof especially in cosmetic and other decorative formulations.

Bismuth oxychloride (BiOCl) pigments are well known in the art and are disclosed for example in U.S. Pat. Nos. 6,743,285, 7,318,862, DE 1 003 377, DE 43 05 280, JP 2001-279126, U.S. Pat. No. 6,579,357, EP 2 584 010, and JP 2012-180403.

Since BiOCl pigments have a high refractive index and a pearl-like or metallic silver lustre, they are employed in paints coatings, plastics, and cosmetic products. However, there is still a need for High Luster (HL) BiOCl pigments in powder form.

Surprisingly, the present invention provides coated BiOCl flakes, which are in powder form and show a high luster. Advantageously, the new pigment powders are dry, liquid-free powders, which are instantly redispersible.

In detail, the invention relates to pigment powders consisting of coated BiOCl flakes, which flakes are selected from a) BiOCl flakes having a coating comprising yellow iron oxide $Fe_2O_3*xH_2O$, optionally a colorant, optionally an adjuvant, and optionally $SiO_2$, b) BiOCl flakes having a coating comprising $SiO_2$, optionally a colorant, and optionally an adjuvant, c) BiOCl flakes having a coating comprising a colorant, $SiO_2$, optionally yellow iron oxide $Fe_2O_3*xH_2O$ or, and optionally an adjuvant, and d) BiOCl flakes having a coating comprising $Fe_3O_4$ and optionally $SiO_2$, to a process for the preparation of the pigment powders, and to the use thereof especially in cosmetic and other decorative formulations.

The above are referred to herein as embodiments 1a), 1b), 1c) and 1d) in the order recited.

The coated BiOCl flakes can be regarded to represent a composite particle which is comprised of a substrate particle of BiOCl, which is covered, optionally in sequence, by the compounds described.

In a preferred embodiment of the invention, the pigment powders consist of coated BiOCl flakes wherein the coatings according to a), b), c) or d) consist of the components described in each case.

A further preferred embodiment of the invention relates to pigment powders consisting of coated BiOCl flakes selected from
a) BiOCl flakes having a first layer comprising yellow iron oxide $Fe_2O_3*xH_2O$, optionally a colorant and optionally an adjuvant, and optionally a second layer comprising $SiO_2$,
b) BiOCl flakes having a layer comprising $SiO_2$,
c) BiOCl flakes having a first layer comprising a colorant, $SiO_2$, optionally yellow iron oxide $Fe_2O_3*xH_2O$, and optionally an adjuvant, and optionally a second layer comprising $SiO_2$ and
d) BiOCl flakes having a first layer comprising $Fe_3O_4$ and optionally a second layer comprising $SiO_2$.

The above are referred to herein as embodiments 2a), 2b), 2c) and 2d) in the order recited.

A particularly preferred embodiment of the invention, the pigment powders consist of coated BiOCl flakes wherein the layers according to a), b), c) or d) consist of the components described in each case.

In particular, preferred variants of the invention are:
a) pigments powders consisting of BiOCl flakes coated with yellow iron oxide $Fe_2O_3*xH_2O$, optionally a colorant, optionally an adjuvant, and optionally $SiO_2$,
b) pigments powders consisting of BiOCl flakes coated with $SiO_2$, optionally a colorant, and optionally an adjuvant,
c) pigments powders consisting of BiOCl flakes coated with a colorant, $SiO_2$, optionally yellow iron oxide $Fe_2O_3*xH_2O$ or, and optionally an adjuvant, and
d) pigments powders consisting of BiOCl flakes coated with $Fe_3O_4$ and optionally $SiO_2$.

Throughout the description, in the examples, and in the claims, yellow iron oxide is referred to as $Fe_2O_3*xH_2O$ as well as FeOOH, wherein x preferably stands for x=0.5 to 1.0, especially 1.

Throughout the description, in the examples, and in the claims, black iron oxide is referred to as $Fe_3O_4$ as well as $(FeO)_{1\pm x}*(Fe_2O_3)_{1\pm x}$, wherein x preferably stands for x=0 to 1.0, especially 0.2 to 1.0 and in particular 0.

A pigment powder consisting of bismuth oxychloride (BiOCl) substrates coated with layers as described above or according to the preferred embodiments differs from existing BiOCl products in that it is comprised of dry (liquid-free) powder and the coated BiOCl flakes have a specific coating composition. The particles are high lustre BiOCl (very thin and uniform flakes) that are instantly redispersible in liquids and also suitable for use in powder mixtures as well. Without a layer according to the invention, the high lustre BiOCl flakes are not redispersible unless specialized methods are applied, which renders them commercially infeasible. The layers provide a barrier and prevent the strong inter-particle adhesion otherwise encountered without treatment.

The combination of silica followed by a silane residue extends the redispersion stability much greater yet, to the point of commercial interest. Thus, an organic after coating may additionally be applied to the coated BiOCl flakes according to the invention. This organic after coating can consist of coupling reagents, such as, for example, organosilanes, organoaluminates, organotitanates and/or zirconates. The coupling agents are preferably organosilanes. Examples of organosilanes are propyltrimethoxysilane, propyltriethoxysilane, isobutyltrimethoxysilane, n-octyltrimethoxysilane, i-octyltrimethoxysilane, n-octyltriethoxysilane, n-decyltrimethoxysilane, dodecyltrimethoxysilane, hexadecyltrimethoxysilane, vinyltrimethoxysilane, preferably n-octyltrimethoxysilane and n-octyltriethoxysilane. Suitable oligomeric, alcohol-free organosilane hydrolysates are, inter alia, the products marketed under the trade name Dynasylan® Hydrosil by Evonik Industries, such as, for example, Dynasylan® Hydrosil 2926, Dynasylan® Hydrosil 2909, Dynasylan® Hydrosil 2907, Dynasylan® Hydrosil 2781, Dynasylan® Hydrosil 2776, Dynasylan® Hydrosil 2627. In addition, oligomeric vinylsilane and also aminosilane hydrolysate is suitable as organic after coating. Functionalised organosilanes are, for example, 3-aminopropyltrimethoxysilane, 3-methacryloxytrimethoxysilane, 3-glycidyloxypropyltrimethoxysilane, beta-(3,4-epoxycyclohexyl)ethyltrimethoxysilane, gamma-isocyanatopropyltrimethoxysilane, 1,3-bis(3-glycidoxypropyl)-1,1,3,3,-tetramethyldisiloxane, ureidopropyltriethoxysilane, preferably 3-aminopropyltrimethoxysilane, 3-methacryloxytrimethoxysilane, 3-glycidyloxypropyltrimethoxysilane, beta-(3,4-epoxycyclohexyl)ethyltrimethoxysilane, gamma-isocyanatopropyltrimethoxysilane. Examples of polymeric silane systems are described in WO 98/13426 and are marketed, for example, by Evonik Industries under the trade name Dynasylan® Hydrosil. The amount of organic after coating can be between 0.2 and 5% by weight, based on the pigment, preferably 0.5 to 2% by weight.

However, the pigment powders of the invention consist preferably of coated BiOCl flakes which do not comprise further coatings other than the coatings described in the embodiments a), b), c) or d). Especially, in the preferred variants of the invention the BiOCl flakes do not comprise additional coatings other than the coatings described in the embodiments a), b), c) or d).

The individual pigment particle of a pigment powder of the invention is comprised of a coated BiOCl flake substrate as a composite of the same composition as the assembly of the particles. Additionally, the new pigment powders show enhanced resistance to UV induced photograying, compared to uncoated BiOCl pigments.

A pigment powder consisting of bismuth oxychloride (BiOCl) substrates coated according to embodiment 1a) or 2a) provides a color which is shifted in the direction towards that of a gold lustre effect product which combines yellow masstone and gold lustre effect. The uniformity of thickness and surface smoothness is sufficient to allow an optical coupling effect which pushes the combined optical thickness (physical thickness of both layers, substrate and coating, multiplied by the effective refractive index) of the composite particle into the range which gives a yellow lustre hue. The hue of the yellow absorption color of the hydrous iron oxide is close to that of the lustre, thus providing a gold lustre effect.

The iron oxide coating introduces a masstone color and a yellow shade (gold) interference effect which has never been reported before for high lustre BiOCl pigments. Compared to other gold pearlescent pigments the effect is sharper and more brilliant, with more of a metallic effect. For example, combinations of blended mixtures of independent particles of yellow iron oxide and BiOCl show a yellow shift of lustre shade of BiOCl. Such a lustre shade is weakly shifted from silver white and results in a much weaker lustre effect.

Furthermore, the deposition of yellow iron oxide as a coated layer of preferably 15% by weight of BiOCl, provides colloidal/mechanical stabilization with or without the addition of another additive. Therefore, the pigment powder can be instantly dispersed in fluids, unlike dry BiOCl without a yellow iron oxide coating. The uniform deposition of yellow iron oxide overcomes the adhesive nature of BiOCl flakes to strongly bond to themselves in dry form.

The combination of yellow iron oxide and silica residue may provide stabilization of the dry powder at lower % yellow iron oxide content near or less than 10%. The presence of a silica exterior treatment also provides a valuable enhancement of the compatibility with aqueous systems by providing a pH neutral surface which does not react adversely with water borne resin systems.

Furthermore, as a precursor, yellow iron oxide can be converted to darker and redder shade masstone color, by heating at low temperatures, i.e. baking at 150 to 500° C., preferably in an inert atmosphere. The new color effect is still showing a high lustre effect with gold interference shade.

Preferred variants of pigment powders consisting of bismuth oxychloride (BiOCl) substrates coated according to embodiment 1a) or 2a) are:

Variant 1

| BiOCl flake substrate | 60-95%, particularly 65 to 95%, preferably 70-92%, especially 80-91% |
|---|---|
| $Fe_2O_3 \cdot xH_2O$ coating | 5-40%, particularly 5 to 35%, preferably 8-30%, especially 9-20% |

Variant 2/Silica Treated

| BiOCl flake substrate | 55-94.99%, especially 60 to 90%, preferably 65-90%, |
|---|---|
| $Fe_2O_3 \cdot xH_2O$ coating | 5-40%, especially 5 to 35%, preferably 5-30% |
| Silica $SiO_2$ | 0.01-5%, especially 3-~5%, preferably 4-~5%, |

Variant 3/Inert Baked

| BiOCl flake substrate | 55-94.98%, especially 55 to 85%, preferably 65% |
|---|---|
| $Fe_2O_3 \cdot xH_2O$ coating | 5 to 35%, preferably 30% |
| Bi metal | 0.01-5%, especially <5%, preferably 3% |
| Carbon | 0.01-5%, especially <5%, preferably 2% |

A pigment powder consisting of bismuth oxychloride (BiOCl) substrates coated according to embodiment 1 b) or 2b) provides high luster BiOCl (very thin and uniform flakes) that are instantly redispersible in liquids and also suitable for use in powder mixtures as well. Without the silica treatment, the high lustre BiOCl flakes are not redispersible unless specialized methods are applied, which renders them commercially infeasible. The silica by itself provides a barrier to avoid the strong inter-particle adhesion otherwise encountered without treatment. The combination of silica followed by a silane residue extends this redispersion stability much greater yet, to the point of commercial interest.

Preferred variants of pigment powders consisting of bismuth oxychloride (BiOCl) substrates coated according to embodiment 1 b) or 2b) are:

Variant 4

| BiOCl flake substrate | 90 to 95% or 80-98%, preferably 80-96%, especially 94-95% |
|---|---|
| $SiO_2$ | 5-10% or 2-20%, especially 4-20%, preferably 5-6% |

A pigment powder consisting of bismuth oxychloride (BiOCl) substrates coated according to embodiment 1c) or 2c) provides high luster BiOCl with a strong masstone color and a strong, smooth and continuous silver white luster effect in application, furthermore with an unusually strong payout in liquid formulations of a wide range of viscosity and molecular polarity and enhanced skin adhesion especially from water based formulations after drying. The pigments of this concept provide a color distinguished in the intensity of brilliance in comparison to combination pigments on other pearlescent substrates such as metal oxide coated on substrates such as mica, silica, synthetic mica, glass flake etc. Furthermore, the performance of these pigments shows enhanced intensity of color and pearlescent effect in comparison to simple blends of dispersed dry high lustre powder particles and dispersed colorants.

The composition can be regarded to represent a composite particle which is comprised of a substrate particle of BiOCl, which is preferably covered or treated in sequence, first by precipitated particles of yellow iron oxide (iron (III) oxide hydrate) to provide colloidal stability (i.e. prevent flocculation), then by adhered particles of colorant, together with or followed by the precipitated particles of silica. The adjuvant substance is adhered by physisorption to the substrate and it also provides adhesion of the colorant particles. The silica precipitate also provides enhanced deposition and enhanced adhesion of the colorant particles onto the high luster BiOCl surface.

Preferred variants of pigment powders consisting of bismuth oxychloride (BiOCl) substrates coated according to embodiment 1c) or 2c) are:
Variant 5

| | |
|---|---|
| BiOCl flake substrate | 57-90%, especially 60 to 85%, preferably 80% |
| $Fe_2O_3*xH_2O$ coating | 0.01-3%, especially <3%, preferably 1% |
| Colorant | 3-20%, particularly 5 to 20%, preferably 5-10% |
| $SiO_2$ | 4-15%, particularly 4 to 15%, preferably 4-6% |
| Adjuvant substance | 0.01-5%, especially <5%, preferably ~3% |

A pigment powder consisting of bismuth oxychloride (BiOCl) substrates coated according to embodiment 1d) or 2d) provides high luster BiOCl darker in masstone and very high in hiding and shows enhanced resistance to UV induced photograying, resulting in very slight darkening under the same exposure conditions that normally induce severe darkening of HL BiOCl. The darker masstone provides a greater contrast in angular dependent viewing, resulting in a higher flop index. Overall the effect remains relatively transparent, i.e. this is a partial step towards a metallic effect, the performance is uniquely intermediate between transparent pearlescent effect and opaque metallic.

The deposition of black iron oxide by itself provides colloidal/mechanical stabilization with or without the addition of silica. The uniform deposition of black iron oxide overcomes the adhesive nature of HL BiOCl flakes to bond to themselves in dry form. Therefore, in some applications there may not be the need to apply both black iron oxide and silica to achieve instant dispersibility. However, the deposition of black iron oxide followed by silica can be advantageous, resulting in greater thermal stability against oxidation. The presence of a silica overcoat provides a chemical resistance when heated in air and helps to prevent undesirable color shift towards lighter and yellower and redder. The temperature induced shift still occurs, but after longer heating duration and at higher temperatures.

The black iron oxide as deposited exhibits magnetic properties similar to other composite flake products, e.g. orienting, aligning and moving in a magnetic field provided from a strong static magnet. This is consistent with at least some degree of chemical purity, crystallinity and uniformity of deposition of $Fe_3O_4$ magnetite.

Preferred variants of pigment powders consisting of bismuth oxychloride (BiOCl) substrates coated according to embodiment 1d) or 2d) are:
Variant 6

| | |
|---|---|
| BiOCl flake substrate | 75-95%, preferably 80-92%, especially 84-91% |
| Black iron oxide $(FeO)_{1\pm x}*(Fe_2O_3)_{1\pm x}$ | 5-20%, preferably 8-17%, especially 9-15% |
| $SiO_2$ | 0-5%, preferably 0-3%, especially 0-1% |

In the foregoing and in the following, unless otherwise indicated, all percentages are by weight based on the total coated BiOCl flakes.

Preferred BiOCl flakes suitable for the invention have a size in the range of the 1-40 μm, preferably 2-35 μm, and in particular 8-20 μm.

Preferably, BiOCl flakes suitable for the invention have a thickness of <100 nm, preferably <80 nm.

Particularly preferred uncoated BiOCl flakes have a thickness in the range of 20-90 nm, especially in the range of 40-80 nm.

Preferably, BiOCl flakes suitable for the invention have an aspect ratio (diameter/thickness ratio) in the range of 50-500. Lateral dimensions are preferably 5 to 20 μm, especially in the range of 10 to 15 μm.

The particle size and particle size distribution can be determined by various methods which are usual in the art. Furthermore, both the particle size and quality can be gauged by optical microscopy. The particle size and the thickness of individual particles can in addition be determined with the aid of SEM (scanning electron microscope) images and by cross-sectional cuttings achieved by laser ablation. In these, particle size and geometrical particle thickness can be determined by direct measurement.

Preferred colorant suitable for the invention are inorganic and organic pigments or dyes, e.g. D&C Red 30, FD&C Blue 1 Aluminum lake, and other water-insoluble pigment particles, FD&C Yellow 3 Aluminum lake, FD&C Red 40 Aluminium lake. In accordance with the method of preparation, the fine particles (preferably less than 5 μm in particle breadth) of any water insoluble colorant such as phthalocyanine blue and green are suitably designated.

The adjuvant substance is preferably selected from non-ionic surfactant molecules based on fatty alkyl chains bound to polyethylene glycol (polyoxyethylene) chains. Variations include but are not limited to ethoxylated fatty amines, ethoxylated fatty esters, ethoxylated fatty alcohols or ethoxylated fatty (alcohol) phosphate esters. Alternatively, the surfactant can be comprised of a mixture of ethoxylated surfactants of various lengths of polyoxyethylene chains and hence various degrees of solubility. The surfactant can also be selected to choose one with a convenient cloud point or low critical solubility temperature, which provides soluble mixtures at lower temperatures and subsequently once heated above the critical temperature, the solubility is decreased and the molecule is precipitated without loss of dispersibility.

As a variation the dry high luster BiOCl powder can be further treated by deposition of metal or metal oxides or metal compounds as coatings in a fluid bed device, e.g. by vapor deposition.

The dry powder high luster can also contain colloidal nano-particles of metals (in elemental form, e.g. bismuth from deposition or reaction of BiOCl using a reducing agent such as $NaBH_4$ etc.) or metal oxides or metal salts, which are processed by a modification of the above procedure. The added particles would be either covered or occluded in the silica deposit. These coatings can also be capped by the addition of a trialkoxy alkyl silane.

The pigment powders of the invention can be prepared by wet-chemical preparation methods. The pigment powders are subsequently spray-dried or oven-dried (temperatures 110° C.) and optionally baked at low temperatures (150-500° C.). These methods are familiar to the person skilled in the art. In the case of wet-chemical application, the corresponding oxides, hydroxides and/or oxide hydrates and optionally colorants and/or adjuvants are deposited on the substrate.

To this end, the flake-form substrates are suspended in a solvent, preferably water, and solutions of the metal salts, colorants and/or adjuvants are added. The oxides, hydroxides and/or oxide hydrates, colorants and/or adjuvants are precipitated onto the substrates.

Suitable starting compounds for the oxides, hydroxides and/or oxide hydrates to be precipitated are the corresponding halides, nitrates and/or sulfates, the corresponding halides and/or nitrates are preferably employed. The oxides, hydroxides and/or oxide hydrates of silicon are preferably applied by means of an aqueous alkali silicate solution or an alkoxy orthosilicate, in particular TEOS (tetraethyl orthosilicate). The metal salt solutions are added simultaneously or successively at a pH which is suitable for hydrolysis of the salts, where the pH is selected so that the metal oxides or hydroxides or oxide hydrates are deposited directly on the substrates. The adjustment of the pH necessary for the precipitation of the respective material and the temperature is familiar to the person skilled in the art.

It is also possible to apply an organic coating, for example, produced from coupling reagents as described in the foregoing. The organic after coating preferably consists of the cross-linked and dehydrated residues of organosilanes. Examples of preferred organosilanes are propyltrimethoxysilane, propyltriethoxysilane, isobutyltrimethoxysilane, n-octyltrimethoxysilane, i-octyltrimethoxysilane, n-octyltriethoxysilane, n-decyltrimethoxysilane, dodecyltrimethoxysilane, hexadecyltrimethoxysilane, vinyltrimethoxysilane, preferably n-octyltrimethoxysilane and n-octyltriethoxysilane.

When comparing with BiOCl dispersions, the new pigment powders consisting of coated BiOCl flakes allow more flexibility in applications.

The pigment powders according to the invention are advantageously employed in color/decorative and personal care cosmetics, such as powders, soaps, surfactant-containing cleansing products, lipsticks, rouge, make-up, care creams, sunscreen compositions, hair treatment products, eye shadow, rouge, cosmetic sticks, pencils, hair care and hair colors such as temporary hair color products, nail care, nail lacquers/polish, and make-up powders of all types. The cosmetic products are distinguished by particularly interesting color effects.

The pigment powders can furthermore be mixed with commercially available state-of-the-art fillers. Fillers which may be mentioned are, for example, uncoated natural and synthetic mica, glass beads or glass powder, nylon powder, polymethylmethacrylate powders, pure or filled melamine resins, talc, glasses, kaolin, oxides or hydroxides of aluminium, magnesium, calcium or zinc, BiOCl, barium sulfate, calcium sulfate, calcium carbonate, magnesium carbonate, carbon, boron nitride and physical or chemical combinations of these substances. There are no restrictions regarding the particle shape of the filler. In accordance with requirements, it can be, for example, flake-form, spherical, needle-shaped, crystalline or amorphous.

The pigment powders according to the invention can of course also be combined in the formulations with cosmetic raw materials and auxiliaries of any type. These include, inter alia, oils, fats, waxes, film formers, surfactants, antioxidants, such as, for example, vitamin C or vitamin E, stabilisers, odour intensifiers, silicone oils, emulsifiers, solvents, such as, for example, ethanol, or ethyl acetate or butyl acetate, preservatives and auxiliaries which generally determine applicational properties, such as, for example, thickeners and rheological additives, such as, for example, bentonites, hectorites, silicon dioxides, Ca silicates, gelatines, high-molecular-weight carbohydrates and/or surface-active auxiliaries, etc.

The formulations comprising the pigment powders according to the invention can belong to the lipophilic, hydrophilic or hydrophobic type. In the case of heterogeneous formulations having discrete aqueous and non-aqueous phases, the pigment powders according to the invention may in each case be present in only one of the two phases or alternatively distributed over both phases.

The pH of the cosmetic formulations can be between 1 and 14, preferably between 2 and 11 and particularly preferably between 5 and 8.

The pigment powders according to the invention may furthermore also be combined with cosmetic active ingredients. Suitable active ingredients are, for example, insect repellents, inorganic UV filters, such as, for example, $TiO_2$, UV A/BC protective filters (for example OMC, B3 and MBC), also in encapsulated form, anti-ageing active ingredients, vitamins and derivatives thereof (for example vitamin A, C, E, etc.), self-tanning agents (for example DHA, erythrulose, inter alia), and further cosmetic active ingredients, such as, for example, bisabolol, LPO, VTA, ectoine, emblica, allantoin, bioflavonoids and derivatives thereof.

Organic UV filters are generally incorporated into cosmetic and other decorative formulations in an amount of 0.5 to 10% by weight, preferably 1 to 8%, and inorganic filters in an amount of 0.1 to 30%.

The pigment powders according to the invention may in addition comprise further conventional skin-protecting or skin-care active ingredients. These may in principle be any active ingredients known to the person skilled in the art. Particularly preferred active ingredients are pyrimidine carboxylic acids and/or aryl oximes.

Application forms of the cosmetic formulations which may be mentioned are, for example: solutions, suspensions, emulsions, PIT emulsions, pastes, ointments, gels, creams, lotions, powders, soaps, surfactant-containing cleansing compositions, oils, aerosols and sprays. Examples of other application forms are sticks, shampoos and shower preparations. Any desired customary excipients, auxiliaries and, if desired, further active ingredients may be added to the preparation.

Ointments, pastes, creams and gels may comprise the customary excipients, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary excipients, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary excipients, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary excipients, such as liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary excipients, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary excipients, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary excipients, such as synthetic oils, such as, for example, fatty acid esters, fatty alcohols, silicone oils, natural oils, such as vegetable oils and oily plant extracts, paraffin oils, lanolin oils, or mixtures of these substances.

The cosmetic preparations may exist in various forms. Thus, they can be, for example, a solution, a water-free preparation, an emulsion or microemulsion of the water-in-oil (W/O) or oil-in-water (O/W) type, a multiple emulsion, for example of the water-in-oil-in-water (W/O/W) type, a gel, a solid stick, an ointment or an aerosol. It is also advantageous to administer ectoines in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Further embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

Solid sticks consist of natural or synthetic waxes and oils, fatty alcohols, fatty acids, fatty acid esters, lanolin and other fatty substances.

If a preparation is formulated as an aerosol, the customary propellants, such as alkanes, fluoroalkanes and chlorofluoroalkanes, are generally used.

Cosmetic formulations having light-protection properties may comprise adjuvants, such as surfactants, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used in the cosmetic field.

The invention thus furthermore also relates to formulations comprising the pigment powders according to the invention in combination with at least one constituent selected from the group of absorbents, astringents, antimicrobial substances, antioxidants, antiperspirants, antifoaming agents, antidandruff active ingredients, antistatics, binders, biological additives, bleaching agents, chelating agents, deodorants, emollients, emulsifiers, emulsion stabilisers, dyes, humectants, film formers, fillers, odour substances, flavour substances, insect repellents, preservatives, anticorrosion agents, cosmetic oils, solvents, oxidants, vegetable constituents, buffer substances, reducing agents, surfactants, propellant gases, opacifiers, UV filters and UV absorbers, denaturing agents, viscosity regulators, perfume and vitamins.

In addition, the pigment powders according to the invention can be used in films and plastics, gift foils, plastic containers and mouldings for all applications known to the person skilled in the art. Suitable plastics for the incorporation of the filler pigments according to the invention are all common plastics, for example thermosets or thermoplastics. The description of the possible applications and the plastics which can be employed, processing methods and additives are given, for example, in RD 472005 or in R. Glausch, M. Kieser, R. Maisch, G. Pfaff, J. Weitzel, Perlglanzpigmente [Pearlescent Pigments], Curt R. Vincentz Verlag, 1996, 83 ff, the disclosure content of which is also incorporated herein. The present pigment powders, especially silica-treated, wax-combined dry high lustre pigment powders, may be used in injection molding processes.

When using the pigment powders in surface coatings and inks, all areas of application known to the person skilled in the art are possible, such as, for example, powder coatings, automobile paints, plastic coatings, printing inks for gravure, offset, screen or flexographic printing.

The new HL BiOCl powder can be incorporated in various coatings systems (Acrylic waterborne, solvent borne, nitrocellulose) for different applications such as plastic coatings, pearl dipping, etc. The results are superior, highly reflective finishes than substrate based effective pigments. The results are comparable to BiOCl dispersions.

The new HL BiOCl powder can be used in various ink systems (water born and solvent borne) and applied with a variety of methods including fluid inks (flexographic, gravure and screen-printing) and paste inks (offset/lithographic) such as Sun Chemical S/B, Superior Printing Ink Offset OPV, etc. In a preferred application it can also be applied via bronzing printing methods as well, taking advantage of the finely divided particles in a free-flowing powder. The powder is also advantageously stable against oxidation unlike powdered aluminum and other metal flakes.

The new HL BiOCl powder can be used in thermoplastic applications such as injection molding, blow molding, rotary molding and calendared sheets. The samples are incorporated at generally 1% into resins such as polypropylene. The resulting plastic chip appeared to be lustrous and very opaque. When the powders are wetted and premixed with wax, the reflective effect is much improved.

When comparing with BiOCl dispersions, BiOCl HL powders allow more flexibility in applications.

Advantageously, the new pigment powders provide effects such as non-particulate texture appearance, continuous luster, texture less appearance, mirror effects, and/or metallic effects in all kinds of applications. The material can also be used in thermoset plastic applications such as button casting or thermoformable cast acrylic sheets. Furthermore, the material is suitable for incorporating into coating formulations for electronics housing such as cell phone covers via spray-coating.

The pigment powders according to the invention are likewise suitable in the above-mentioned areas of application for use in blends with organic dyes and/or pigments, such as, for example, transparent and opaque white, coloured and black pigments, and with flake-form iron oxides, BiOCl, organic pigments, holographic pigments, LCPs (liquid crystal polymers) and conventional transparent, coloured and black lustre pigments based on metal oxide-coated flakes based on mica, glass, $Al_2O_3$, $Fe_2O_3$, $SiO_2$, metal flakes, etc.

The pigment powders according to the invention are furthermore suitable for the preparation of flowable pigment compositions and dry preparations comprising the pigment powders, binders and optionally one or more additives. Dry preparations is also taken to mean preparations which comprise from 0 to 8% by weight, preferably from 2 to 8% by weight, in particular from 3 to 6% by weight, of water and/or a solvent or solvent mixture. The dry preparations are preferably in the form of pellets, granules, chips, sausages or briquettes and have particle sizes of 0.2-80 mm. The dry preparations are used, in particular, in the preparation of printing inks and in cosmetic formulations.

The following examples below are intended to illustrate the invention, but without restricting it. Percentages are by weight and all temperatures are set forth in degrees Celsius; unless otherwise indicated.

In the foregoing, in the examples, and in the claims, yellow iron oxide is referred to as FeOOH as well as $Fe_2O_3*xH_2O$, wherein x preferably stands for x=0.5 to 1.0, especially 1.

In the foregoing, in the examples, and in the claims, black iron oxide is referred to as $(FeO)_{1\pm x}*(Fe_2O_3)_{1\pm x}$. as well as $Fe_3O_4$, wherein x preferably stands for x=0 to 1.0, especially 0.2 to 1.0 and in particular 0.

EXAMPLES

Preparation of Gold Lustered Dry Powder High Lustre BiOCl Composite Pigment

The iron oxide coating introduces a masstone color and a yellow shade (gold) interference effect which has never been reported before for high lustre BiOCl pigments. Compared to other gold pearlescent pigments the effect is sharper and more brilliant, with more of a metallic effect. Furthermore, it provides enhanced protection against UV induced darkening and also allows easy redispersion.

Example 1

A slurry of 100 g of high lustre BiOCl flakes (thickness~60 nm; particle size 8-20 μm) which is washed free of reaction by-products (salts and surfactant) is brought to a concentration of 3 wt % in deionized water. The temperature is raised to 75 deg C. with constant stirring, vigorous enough to maintain uniform suspension and disperse the feed solutions throughout the reaction vessel. A solution of 85 g of ferric ammonium sulfate dodecahydrate in 300 mL of deionized water is fed via submerged inlet tube into the slurry, allowing the pH to fall from neutral pH to 3.0 over 30-45 minutes during the initial feed rate. The rest of the solution is delivered over 3 hours while maintaining pH near 3.0 by simultaneously co-fed with 5% ammonia solution. The slurry color changes from pearlescent silver to gold. Thereafter a solution of dilute sodium water glass containing 5.5% of SiO2 is slowly delivered over about 4 hours until pH 6.0 is reached. The slurry is continued under agitation and heating to maintain suspension and temperature briefly and then allowed to sediment. The supernatant is decanted to remove by-products from the mother liquor (salt water) and replaced by equal volumes of deionized water. After repeating the sedimentation, decant and backfill process several times, the slurry is allowed to be settled and decanted further to reach 30% by weight and then submitted to spray-drying at 30 g per hour. The gold colored powder is comprised of a microscopic mechanical mixture composite of 100 g of BiOCl, 15 g of yellow iron oxide (as FeOOH) and 5 g of amorphous silica. The product is finely divided and can be employed without further handling as a specialty colorant in many applications.

Example 2

Procedure in example 1 is repeated but uses 112 grams of ferric ammonium sulfate dodecahydrate instead of 85 g and omits the final neutralization and deposition of SiO2, producing a composite pigment in powder form comprised 100 g of BiOCl and 20 g of iron oxide as FeOOH.

Example 3

Procedure in example 2 is repeated using 140 grams of ferric ammonium sulfate dodecahydrate instead of 85 g, producing a composite pigment in powder form comprised 100 g of BiOCl, 25 g of iron oxide as FeOOH.

Example 4

Procedure in example 2 is repeated using 168 grams of ferric ammonium sulfate dodecahydrate producing a composite pigment in powder form comprised 100 g of BiOCl, 30 g of iron oxide as FeOOH.

Example 5

Procedure in example 2 is repeated using 225 grams of ferric ammonium sulfate dodecahydrate producing a composite pigment in powder form comprised 100 g of BiOCl, 40 g of iron oxide as FeOOH.

Example 6

Procedure in example 2 is repeated using 56 grams of ferric ammonium sulfate dodecahydrate producing a composite pigment in powder form comprised 100 g of BiOCl, 10 g of iron oxide as FeOOH.

Example 7

Procedure in example 2 is repeated, but instead of feeding ferric ammonium sulfate, a~300 mL aqueous solution of ferric nitrate nonahydrate 72 g admixed with ammonium nitrate 11.5 g and adjusted to pH 2.5±0.5 with ammonia, is employed, generating the same composition.

Example 8

Procedure in example 2 is repeated, but instead of feeding ferric ammonium sulfate, a~300 mL aqueous solution of ferric chloride (calculated as anhydrous) 31 g admixed with ammonium chloride 6 g and adjust to pH 2.5±0.5 with ammonia, is employed.

Example 9

Procedure in example 2 is repeated, but instead of feeding ferric ammonium sulfate, a~300 mL aqueous solution of ferrous sulfate heptahydrate 47 g admixed with ammonium sulfate 19 g and neutralized to pH 2.5±0.5 with ammonia, is employed along with feeding compressed air.

Example 10

Procedure in example 2 is repeated, but instead of feeding ferric ammonium sulfate, a ~300 mL aqueous solution of ferric sulfate hydrate 46 g is employed.

Example 11

Procedure in example 1 is repeated at 85 degrees Celsius instead of 75.

Example 12

Procedure in example 1 is repeated using 150 grams of high luster BiOCl flakes.

Example 13

Procedure in example 1 is repeated using 50 grams of high luster BiOCl flakes.

Example 14

Procedure in example 1 is repeated replacing 5% ammonia solution with 5% NaOH solution.

Example 15

Procedure in example 1 is repeated but instead of washing by decanting and back-filling and spray-drying, the final slurry is filtered and washed several times and then oven dried at 110° C., followed by sieving to produce a finely divided powder.

Example 16

A slurry containing 75 g of HL BiOCl is transferred to a 3-neck round bottom flask. Nine hundred milliliters (900 ml) of deionized water are added to the flask and stirred at 250 rpm for 60 minutes. To this slurry 28 g of ferric ammonium sulfate dodecahydrate [$NH_4Fe(SO_4)_2$ $12H_2O$], 5 g of magnesium sulfate heptahydrate [$MgSO_4$ $7H_2O$] and 40 g urea are added and stirred for another 30 minutes (the pH of slurry is around 3). Temperature of the slurry is raised in 30 min to reflux and continued to reflux for another 60 minutes while stirring. By this time, the slurry turns to a gold yellow color. Heating is stopped and the material is allowed to cool down to room temperature. The sample is filtered, washed with deionized water and dried at 110 C overnight. Dried powder is screened with a 45 micrometer sieve.

Example 17

A subsequent variation to provide a darkened masstone color is to bake the finely divided powder, from any of the above examples, at low temperatures, 200 to 500° C. under inert atmosphere such as nitrogen, or argon etc. This converts some of the organic substances to carbon black and partially converts some of the BiOCl on the surface to crystalline Bi metal and possibly partially converts some of the iron (III) oxide hydrate (yellow) to red ($Fe_2O_3$/hematite) by dehydration and/or black iron oxide ($Fe_3O_4$/magnetite) by partial reduction.

Preparation of Colorant Combination Dry Powder High Luster BiOCl Composite Pigment The color combination coating introduces a masstone color and a Silver lustre effect BiOCl pigments. This effect cannot achieve by a mechanical mixture of the two components. This surprisingly also increases the tint strength of the colorant and in some cases very little additional additives are needed to provide a commercially interesting cosmetic formulation.

Example 1

A slurry of 100 g of high luster (HL) BiOCl flakes (thickness~60 nm; particle size 8-20 μm) which is washed free of reaction by-products (salts and surfactant) is brought to a concentration of 3 wt % in deionized water. The temperature is raised to 75 degrees C. with constant stirring, vigorous enough to maintain uniform suspension and disperse the feed solutions throughout the reaction vessel. A solution of 6.6 g ferric ammonium sulfate dodecahydrate in 40 millilitres of deionized water is fed via submerged inlet tube into the slurry, allowing the pH to fall from neutral pH to 2.5 over 30-45 minutes. The rest of the solution is delivered while maintaining pH near 2.5 by simultaneously co-fed with 5% ammonia solution. The addition of 10 grams of colorant D&C Red 30 is accomplished by first dispersing the colorant in 80 ml of propylene glycol by sonication and then transferring it to the aqueous suspension of HL BiOCl treated with iron oxide hydrate. The mixture is then stirred for 15 minutes and 2.3 grams of fatty amine ethoxylate surfactant is added to the slurry. After another 15 minutes of mixing a 350 ml dilute sodium silicate solution, containing 6.0 grams of SiO2, is slowly delivered until pH 6.0. The rest of the solution is delivered while maintaining pH of slurry at 6.0 with 5% HCl solution. The slurry is continued under agitation and heating to maintain suspension and temperature briefly and then allowed to sediment. The supernatant is decanted to remove by-products from the mother liquor (salt water) and replaced by equal volumes of deionized water. After repeating the sedimentation, decant and backfill process several times, the slurry is allowed to be settled and decanted further to reach 30% by weight and then submitted to spray-drying at 30 g per hour. The pink colored powder is comprised of a microscopic mechanical mixture composite of 100 g of BiOCl, 1.2 g of yellow iron oxide (as FeOOH), 10.0 g of D&C Red 30 and 6 g of amorphous silica. The product is finely divided and can be employed without further handling as a specialty colorant in many applications.

Example 2

A slurry of 100 g of high luster BiOCl flakes (thickness~60 nm; particle size 8-20 μm) which is washed free of reaction by-products (salts and surfactant) is brought to a concentration of 3 wt % in deionized water. The temperature is raised to 75 degrees C. with constant stirring, vigorous enough to maintain uniform suspension and disperse the feed solutions throughout the reaction vessel. At this stage the pH of slurry is typically around 5.5. The addition of 10 grams of colorant D&C Red 30 is accomplished by first dispersing the colorant in 80 ml of propylene glycol by sonication and then transferring it to the aqueous suspension of HL BiOCl. After another 30 minutes of mixing a 350 ml dilute sodium silicate solution, containing 6.0 grams of $SiO_2$, is slowly delivered until pH 6.0. The rest of the solution is delivered while maintaining pH of slurry at 6.0 with 5% HCl solution. The slurry is continued under agitation and heating to maintain suspension and temperature briefly and then allowed to sediment. The supernatant is decanted to remove by-products from the mother liquor (salt water) and replaced by equal volumes of deionized water. After repeating the sedimentation, decant and backfill process several times, the slurry is allowed to be settled and decanted further to reach 30% by weight and then submitted to spray-drying at 30 g per hour. The pink colored powder is comprised of a microscopic mechanical mixture composite of 100 g of BiOCl, 10.0 g of D&C Red 30 and 6 g of amorphous silica. The product is finely divided and can employed without further handling as a specialty colorant in many applications.

Example 3

Procedure in example 1 is repeated but used 5.0 grams of D&C Red 30 instead of 10 g producing a composite pigment in powder form comprised 100 g of BiOCl, 5 g of D&C Red 30 and 6 g of amorphous silica.

Example 4

Procedure in example 1 is repeated using 20.0 grams of D&C Red 30 instead of 10 g, producing a composite pigment in powder form comprised 100 g of BiOCl, 20 g of D&C Red 30 and 6 g of amorphous silica.

Example 5

Procedure in example 1 is repeated, but instead of feeding ferric ammonium sulfate, a~40 mL aqueous solution of ferric nitrate nonahydrate 6 g admixed with ammonium nitrate 1 g is employed, generating the same composition.

Example 6

Procedure in example 1 is repeated, but instead of feeding ferric ammonium sulfate, a~40 mL aqueous solution of ferric chloride (calculated as anhydrous) 2.4 g admixed with ammonium chloride 0.5 g and adjust to pH 2.5±0.5 with ammonia, is employed.

Example 7

Procedure in example 1 is repeated, but instead of feeding ferric ammonium sulfate, a~40 mL aqueous solution of ferrous sulfate heptahydrate 3.6 g admixed with ammonium sulfate 1.5 g and neutralized to pH 2.5±0.5 with ammonia, is employed along with feeding compressed air.

Example 8

Procedure in example 1 is repeated, but instead of feeding ferric ammonium sulfate, a~40 mL aqueous solution of ferric sulfate hydrate 3.6 g is employed.

Example 9

Procedure in example 1 is repeated at 85 degrees Celsius instead of 75.

Example 10

Procedure in example 1 is repeated using 150 grams of high luster BiOCl flakes and adjusting weights of other chemicals to maintain the composition.

Example 11

Procedure in example 1 is repeated using 50 grams of high luster BiOCl flakes and adjusting weights of other chemicals to maintain the composition.

Example 12

Procedure in example 1 is repeated replacing 5% ammonia solution with 5% NaOH solution.

Example 13

Procedure in example 1 is repeated replacing propylene glycol with n-Propyl alcohol.

Example 14

Procedure in example 1 is repeated replacing propylene glycol with glycerol.

Example 15

Procedure in example 1 is repeated replacing propylene glycol with aqueous solution of fatty acid ester or fatty alcohol ethoxylate non-ionic surfactant.

Example 16

Procedure in example 1 is repeated replacing fatty amine ethoxylate with fatty acid ester ethoxylate or fatty alcohol ether ethoxylate, especially those with cloud-points above room temperature.

Example 17

Procedure in example 1 is repeated replacing fatty amine ethoxylate or ether ethoxylate with fatty acid ester propoxylate or fatty alcohol ether propoxylate, especially those with cloud-points above room temperature . . . .

Example 18

Procedure in example 1 is repeated replacing silica solution with trialkoxy alkyl silanes.

Example 19

Procedure in example 1 is repeated but fatty amine ethoxylate is added to HL crystal slurry together with D&C Red 30 and propylene glycol.

Example 20

Procedure in example 1 is repeated but organic colorant Blue is added to HL crystal slurry together with D&C Red 30 and propylene glycol.

Example 21

Procedure in example 2 is repeated but organic colorant D&C Red 30 is replaced with FD&C Blue 1 Aluminum Lake.

Example 22

Procedure in example 2 is repeated but organic colorant D&C Red 30 is replaced with FD&C Yellow 5 Aluminum Lake.

Example 23

Procedure in example 2 is repeated but organic colorant D&C Red 30 is replaced with FD&C Red 40 Aluminum Lake.

Example 24

Procedure in example 1 is repeated replacing sonication with high speed rotor stator agitation.

Example 25

Procedure in example 1 is repeated replacing D&C Red 30 with pigmentary carbon black.

Example 26

Procedure in example 1 is repeated but instead of washing by decanting and back-filling and spray-drying, the final slurry is filtered and washed several times and then oven dried at 110 C, followed by sieving to produce a finely divided powder.

Example 27

A subsequent variation to provide a darkened masstone color is to bake the finely divided powder at low temperatures, 200 to 500° C. under inert atmosphere such as nitrogen, or argon etc. This converts some of the organic substances to carbon black and partially converts some of the BiOCl on the surface to crystalline Bi metal. This is a preferred condition to be applied when the colorant is carbon black.

Preparation of Silver Lustered Dry Powder High Luster BiOCl Composite Pigment

The silica coating provides a sufficient colloidal and mechanical stability which allows easy redispersion in formulations and use in a fluidized-bed application for treatments. It provides a universal compatibility with wide range of formulations including water-borne, solvent-borne and oil based. A distinct advantage compared to High Luster BiOCl dispersions is an extended shelf-life.

Example 1

A slurry of 100 g of high luster (HL) BiOCl flakes (thickness~60 nm; particle size 8-20 μm) which is washed free of reaction by-products (salts and surfactant) is brought to a concentration of 3 wt % in deionized water. The temperature is raised to 70 degrees C. with constant stirring, vigorous enough to maintain uniform suspension and disperse the feed solutions throughout the reaction vessel. A 350 ml dilute sodium silicate solution, containing 6.0 grams of $SiO_2$, is slowly delivered until pH of the slurry reached 6.3. The rest of the solution is delivered while maintaining pH at 6.3 with 5% HCl solution. Upon completion of the delivery of sodium silicate solution, the slurry is continued under agitation and heating to maintain suspension and temperature for 30 minutes and then allowed to sediment. The supernatant is decanted to remove by-products from the mother liquor (salt water) and replaced by equal volumes of deionized water. After repeating the sedimentation, decant and backfill process several times, the slurry is allowed to be settled and decanted further to reach 30% by weight and then submitted to spray-drying at 30 g per hour. The white powder is comprised of a microscopic mechanical mixture composite of 100 g of BiOCl and 6 g of amorphous silica. Examination of the powder particles by electron microscope shows that flake particles are at least partially coated by the silica. The product is finely divided and can be employed without further handling as a specialty pigment in many applications.

Example 2-3

Procedure in example 1 is repeated but used only 4 grams and 5 grams of SiO2 respectively producing a composite pigment in powder form.

Example 4-6

Procedure in example 1 is repeated but used 8, 10 and 15 grams of $SiO_2$ respectively producing a composite pigment in powder form.

Example 7

Procedure in example 1 is repeated but used pH 5.0 instead of 6.3 producing a composite pigment in powder form.

Example 8-10

Procedure in example 1 is repeated but used pH 7.0, 7.5 or 8.0 instead of 6.3 producing a composite pigment in powder form.

Example 11

Procedure in example 1 is repeated but the slurry is filtered, washed three times and oven dried at 110 C overnight instead of spray drying producing a composite pigment in powder form.

Example 12-15

Procedure in example 1 is repeated at 65, 75, 80 and 85 degrees Celsius respectively instead of 70 degrees Celsius.

Example 16

Procedure in example 1 is repeated using 150 grams of high luster BiOCl flakes and delivering 9 g of $SiO_2$.

Example 17

Procedure in example 1 is repeated using 50 grams of high luster BiOCl flakes and delivering 3 g of $SiO_2$.

Example 18

Procedure in example 1 is repeated replacing 5% HCl solution with 5% H2SO4 solution.

Example 19

Procedure in example 1 is repeated replacing 5% HCl solution with 5% HNO3 solution.

Example 20

A variation of the product in example 1 is produced by adding a silane to the slurry before it is allowed to settle. In this example an alkyl trialkoxy silane at 1 to 5% per weight of BiOCl is slowly delivered into the water suspension after the completion of silica layer. The alkyl group in silane can consist of methyl, n-propyl or n-octyl, with preference to the latter two. Upon completion of the delivery of silane, the slurry is continued under agitation and heating to maintain suspension and temperature for 30 minutes and then allowed to sediment. The supernatant is decanted to remove by-products from the mother liquor (salt water) and replaced by equal volumes of deionized water. After repeating the sedimentation, decant and backfill process several times, the slurry is allowed to be settled and decanted further to reach 30% by weight and then submitted to spray-drying at 30 g per hour. Resulting white powder is finely divided and can be employed as a specialty pigment in many applications.

Example 21

Another method to produce the material is to use tetraethyl orthosilicate (TEOS) as the silicon source. In this procedure, HL BiOCl crystals are allowed settled and the supernatant is decanted off. Then the crystals are transferred into ethyl acetate (EA) and mixed with a solution of octyl hydroxyl stearate (OHS) and stir to get water and EA into octyl hydroxyl stearate phase. Ethanol is added to the mixture and crystals settle. OSH is decanted off with EA and residue water. Ethanol is added to re-suspend the crystals and required amount of TEOS is added to match the amount of $SiO_2$ desired. An alcohol water solution is added slowly to hydrolyze TEOS to form an $SiO_2$ layer. More water is added and the crystals settle. Supernatant is decanted off to remove alcohol and add water and stirred to produce a uniform slurry. The material is filtered washed and oven dried or spray dried to produce a finely divided powder.

Example 22

As a variation, the dry high luster BiOCl powder is further treated by deposition of metal or metal oxides or metal compounds as coatings in a fluid bed device, e.g. by vapor deposition.

Example 23

The dry powder high luster can also contain colloidal nano-particles of metals (in elemental form, e.g. bismuth from deposition or reaction of BiOCl using a reducing agent such as $NaBH_4$ etc.) or metal oxides or metal salts, which are processed by a modification of the above procedure. The added particles would be either covered or occluded in the silica deposit. These coatings can also be capped by the addition of a trialkoxy alkyl silane.

Example 24

A subsequent variation to provide a darkened masstone color would be to bake the finely divided powder, from any of the above examples, at low temperatures, 200 to 500° C. under inert atmosphere such nitrogen, or argon etc. This converts some of the organic substances to carbon black and partially converts some of the BiOCl on the surface to crystalline Bi metal.

Preparation of Black Iron Oxide Coated Dry Powder High Luster BiOCl Composite Pigment Black iron oxide coating introduces a dark grey masstone color which enhances the flop of luster effect. This effect cannot achieve by a mechanical mixture of the two components. This surprisingly provides darker masstone and higher hiding which more closely emulates a metallic luster effect. Additional benefit is the enhanced UV stability against discoloration.

Example 1

A slurry of 100 g of high luster (HL) BiOCl flakes (thickness~60 nm; particle size 8-20 μm) which is washed free of reaction by-products (salts and surfactant) is dispersed in 1000 ml deionized (DI) water in a 3-neck round-bottom flask and agitated at 250 rpm. Eighty-nine grams of ferrous sulfate heptahydrate ($FeSO_4.7H_2O$), 20 g of magnesium sulfate heptahydrate ($MgSO_4.7H_2O$), 16 grams of potassium nitrate ($KNO_3$) and 150 grams of urea are added to the above slurry and stirred for 45 minutes. The slurry is slowly heated to reflux in about 90 minutes while agitating at 300 rpm. Heating and stirring is continued for another 60 minutes. The slurry color changed from light gray to gray and then to black. Agitation is reduced to 135 rpm, heating is stopped and the slurry is allowed to cool down to room temperature. The material is filtered, washed 3 times with DI water and dried at 110 C in an inert atmosphere for 10 hours. Dried material is sieved with 45 um screen to obtain a microscopic mechanical mixture composite of 100 g of BiOCl, 25 g of black iron oxide (as $Fe_3O_4$). The product is finely divided and can be employed without further handling as a specialty colorant in many applications.

Example 2

Procedure in example 1 is repeated but optional outside silica layer is deposited by means of delivering a sodium silicate solution while maintaining pH of the slurry at 6 by cofeeding a dilute hydrochloric acid solution.

Example 3

Procedure in example 2 is repeated but uses tetraethyl orthosilicate (TEOS) as the silica source. In this procedure, HL BiOCl crystals are allowed settled and the supernatant is decanted off. Then the crystals are transferred into ethyl acetate (EA) and mixed with a solution of octyl hydroxyl stearate (OHS) and stirred to get water and EA into octyl hydroxyl stearate phase. Ethanol is added to the mixture and crystals settle. OSH is decanted off with EA and residue water. Ethanol is added to re-suspend the crystals and required amount of TEOS is added to match the amount of $SiO_2$ desired. An alcohol water solution is added slowly to hydrolyze TEOS to form an $SiO_2$ layer. More water is added and the crystals settle. Supernatant is decanted off to remove alcohol and water is added and stirred to produce a uniform slurry.

Example 4

Procedure in example 1 is repeated but uses a combination of soluble components of ferrous and ferric salts fed all at once and gradually deposited by urea decomposition.

Example 5

Procedure in example 2 is repeated but use concurrent feeds of the iron salt solutions and alkali hydroxides, thus maintaining a relatively high pH.

Example 6

Procedure in example 1 is repeated but uses potassium persulfate ($K_2S_2O_8$) in lieu of nitrate as an oxidant to induce ferric oxide deposition. It is also possible to use other oxidizing agents such as hydrogen peroxide, sodium hypochlorite, sodium chlorite, sodium chlorate, sodium perchlorate etc.

Example 7

Yellow iron oxide layer is deposited using a solution of ferric ammonium sulfate while maintaining slurry pH at 3.0 with a 5% ammonia solution. After filtering, washing and drying, the dried pigment is heated at 400° C. under a flow of 4% H/argon to obtain a black iron oxide coated HL BiOCl powder. Optional silica outside silica layer can also be employed.

Example 8

Procedure in example 7 is repeated but uses a ferric chloride solution in place of ferric ammonium sulfate to generate a red iron oxide layer instead of a yellow iron oxide.

Example 9

Procedure in example 1 is repeated but the slurry is concentrated and fed to a spray-dryer instead of oven drying. The spray-dried powder is a finely-divided finished good which can be directly packaged without further mechanical treatment.

Example 10

Procedure in example 1 is repeated but the washing and dewatering is done by filter press. Filtration can also be accomplished using a belt filter or a drum filter resulting in a wet-cake.

Examples of Cosmetic Applications with New High Luster (HL) BiOCl Powders

1. Eye Shadow Gel

| Ingredients | INCI (US) | [%] |
|---|---|---|
| A | | |
| Water, demineralized | WATER | 73.00 |
| New HL BiOCl Powder (Black or Blue) | | 10.00 |
| Carbopol ® Ultrez 10 | CARBOMER | 0.30 |
| B | | |
| Water, demineralized | WATER | 13.00 |
| Glycerol, anhydrous | GLYCERIN | 2.00 |
| RonaCare ® Triethanolamine-Replace by 108372 Triethanolamine, EMPROVE ® exp. | TRIETHANOLAMINE | 0.70 |
| Germaben II | PROPYLENE GLYCOL (AND) DIAZOLIDINYL UREA (AND) METHYLPARABEN (AND) PROPYLPARABEN | 1.00 |

The range of the new HL BiOCl in the formulation can be 10-15% by weight.

2. Loose Powder Eye Shadow

| Ingredients | INCI (US) | [%] |
|---|---|---|
| A | | |
| Supra H | TALC | 38.80 |
| New HL BiOCl Powder (Silverwhite) | | 20.00 |
| Colorona ® Magenta | MICA (AND) TITANIUM DIOXIDE (AND) CARMINE | 20.00 |
| Dry Flo PC | ALUMINUM STARCH OCTENYLSUCCINATE | 10.00 |
| Kaolin | KAOLIN | 4.00 |
| Magnesium Stearate. | MAGNESIUM STEARATE | 2.00 |
| Propylparaben | PROPYLPARABEN | 0.20 |
| B | | |
| Eutanol G | OCTYLDODECANOL | 5.00 |

3. Lipstick

| Ingredients | INCI (US) | [%] |
|---|---|---|
| A | | |
| Castor Oil | RICINUS COMMUNIS (CASTOR) SEED OIL | 43.85 |
| Candelilla Wax | EUPHORBIA CERIFERA (CANDELILLA) WAX | 5.70 |
| Carnauba Wax | COPERNICIA CERIFERA (CARNAUBA) WAX | 1.80 |
| Ozokerite Wax SP 1028P | OZOKERITE | 1.50 |
| Microcrystalline Wax White 1275 W | MICROCRYSTALLINE WAX | 3.00 |
| Myritol 312 | CAPRYLIC/CAPRIC TRIGLYCERIDE | 16.00 |
| Blandol | MINERAL OIL | 2.00 |
| Ceraphyl 847 | OCTYLDODECYL STEAROYL STEARATE | 5.00 |
| Eutanol G | OCTYLDODECANOL | 5.00 |
| OHlan | HYDROXYLATED LANOLIN | 1.00 |
| Propylparaben | PROPYLPARABEN | 0.10 |
| Oxynex ® K liquid | PEG-8 (AND) TOCOPHEROL (AND) ASCORBYL PALMITATE (AND) ASCORBIC ACID (AND) CITRIC ACID | 0.05 |
| B | | |
| Xirona ® Le Rouge | IRON OXIDES (AND) SILICA | 4.00 |
| New HL BiOCl Powder (Silverwhite) | | 11.00 |

4. Lip Gloss

| Ingredients | INCI (US) | [%] |
|---|---|---|
| A | | |
| Indopol H-100 | POLYBUTENE | 30.00 |
| Versagel ® ME 750 | HYDROGENATED POLYISOBUTENE (AND) ETHYLENE/PROPYLENE COPOLYMER (AND) BHT | 24.00 |
| Beeswax Yellow | BEESWAX | 4.00 |
| Myritol 312 | CAPRYLIC/CAPRIC TRIGLYCERIDE | 6.00 |
| Jarplex SB 10 | BUTYROSPERMUM PARKII (SHEA) BUTTER | 3.00 |

-continued

| Ingredients | INCI (US) | [%] |
|---|---|---|
| Castor Oil | RICINUS COMMUNIS (CASTOR) SEED OIL | 8.85 |
| Cetiol ® 868 | ETHYLHEXYL STEARATE | 10.00 |
| LexFeel Shine | PROPYLENE GLYCOL DIBENZOATE | 4.00 |
| Oxynex ® ST | DIETHYLHEXYL SYRINGYLIDENE MALONATE | 0.10 |
| Oxynex ® K liquid | PEG-8 (AND) TOCOPHEROL (AND) ASCORBYL PALMITATE (AND) ASCORBIC ACID (AND) CITRIC ACID | 0.05 |
| Propylparaben | PROPYLPARABEN | 0.10 |
| B | | |
| New HL BiOCl Powder (Pink or Black) | | 9.90 |

5. Shampoo

| Ingredients | INCI (US) | [%] |
|---|---|---|
| A | | |
| New HL BiOCl Powder (Gold or Black) | | 1.00 |
| Water, demineralized | WATER | 43.40 |
| Carbopol ® Aqua SF-1 Polymer | Carbopol ® Aqua SF-1 Polymer | 8.00 |
| Texapon NSO UP | WATER (AND) SODIUM LAURETH SULFATE | 40.00 |
| Sodium Hydroxide, 10% | WATER (AND) SODIUM HYDROXIDE | 0.00 |
| B | | |
| Tego ® Betain F 50 | COCAMIDOP ROPYL BETAINE | 5.60 |
| Proteol O.A.T. | SODIUM LAUROYL OAT AMINO ACIDS | 1.00 |
| Euxyl K 500 | WATER (AND) DIAZOLIDINYL UREA (AND) SODIUM BENZOATE (AND) POTASSIUM SORBATE | 1.00 |
| Fragrance (q.s.) | FRAGRANCE | 0.00 |
| Dye stuff solution (q.s.) | | 0.00 |

6. Nail Polish

| Ingredients | INCI (US) | [%] |
|---|---|---|
| New HL BiOCl Powder (Gold) | | 2.00 |
| Dispersion of cosmetic colors in nitrocell. lacquer (q.s.) | | 0.00 |
| Nail lacquer Base 12897 | ETHYL ACETATE (AND) BUTYL ACETATE (AND) NITROCELLULOSE (AND) PHTHALIC ANHYDRIDE/TRIMELLITIC ANHYDRIDE/GLYCOLS COPOLYMER (AND) ACETYL TRIBUTYL CITRATE (AND) ISOPROPYL ALCOHOL (AND) STEARALKONIUM HECTORITE (AND) ADIPIC ACID/NEOPENTYL GLYCOL/TRIMELLITIC ANHYDRIDE COPOLYMER | 98.00 |

7. Pressed Eye Shadow

| Ingredients | INCI (US) | [%] |
|---|---|---|
| A | | |
| New HL BiOCl Powder (Gold) | | 30.00 |
| Parteck ® LUB Talc | TALC | 50.55 |
| Parteck ® LUB MST | MAGNESIUM STEARATE | 2.55 |
| Potato Starch | POTATO STARCH | 7.65 |
| B | | |
| Isopropyl Stearate | ISOPROPYL STEARATE | 7.85 |
| Cetyl Palmitate | CETYL PALMITATE | 0.45 |
| Ewalin 1751 | PETROLATUM | 0.45 |
| C | | |
| Euxyl ® PE 9010 | PHENOXYETHANOL (AND) ETHYLHEXYL GLYCERIN | 0.50 |

8. Serum with New HL BiOCl Pigment

| Ingredients | INCI (US) | [%] |
|---|---|---|
| A | | |
| Water, demineralized | WATER | ad 100 |
| Triplex ® III | DISODIUM EDTA | 0.05 |
| RonaCare ® Ectoin | ECTOIN | 0.25 |
| Carbopol ® Ultrez 20 | ACRYLATES/C10-30 ALKYL ACRYLATE CROSSPOLYMER | 0.80 |
| Preservatives | PRESERVATIVES | q.s. |
| 1,2-Propandiol | PROPYLENE GLYCOL | 2.00 |
| B | | |
| RonaCare Triethanolamine | TRIETHANOLAMINE | 1.00 |
| C | | |
| New HL BiOCl Powder (Silverwhite) | | 1.00 |

9. Dip or Spray Coated Pearl Beads

Here is an example of using new HL BiOCl powder in coatings applications. It is obtained by dispersing the new HL BiOCl powder to a nitrocellulose coatings system. A person skilled in the art knows how to carry out the steps (wetting/deaerating the powder followed by suitable mixing) to achieve a well dispersed coating formulation. The composition of the formulation shown below is final formulation that is ready to be sprayed or dipped onto plastic or glass bead substrates. Nitrocellulose is a preferred film-forming resin, but other options are possible, especially as combinations. The nitrocellulose resin content can be replaced in part by other solids such as other resins and transparent extenders to enhance features such as gloss and surface smoothness. The solvent can also be optionally replaced with other solvents to slow down or speed up evaporation or with other liquids such as plasticizers for enhanced gloss and flexibility, depending on the coating method, dip or spray. The resulting bead shows a very smooth and intense pearl effect that mimics natural pearls. The concentration of the new HL BiOCl powder in the formulation can vary depending on the final appearance required. Other colorants, either solvent soluble dyes or insoluble particle dispersions, can be added in low concentrations e.g. <1% to the formulation to achieve the desired color. Other optional additives such as UV absorbers can be included at low concentrations e.g. <1%, with the intent to protect the bismuth oxychloride flakes against UV light induced darkening. For optimum results, multiple thin layers of coatings are sprayed repeatedly to achieve a deep and sharp lustered pearl effect. Proper viscosity (lower for spraying and higher for dipping) should be maintained by selection of suitable viscosity grades of nitrocellulose resin.

| Ingredients | Description | [%] |
|---|---|---|
| HL BiOCl Powder (SilverWhite) | Bismuth oxychloride and silica | 0.1 to 3 |
| Resin | Nitrocellulose RS ⅛ to 15 sec viscosity grades | 5 to 15 |
| Solvent | Isopropanol | 2 to 6 |
| Solvent | n-Butyl Acetate | 76 to 95 |

All new HL BiOCl powders (Silverwhite, Black/Silver, Gold with various shades, Blue, Pink) can be used in the above formulations with minor formulation adjustments.

The results are superior, highly reflective products than substrate based effective pigments. Generally, more metallic and higher reflective appearance and less particulates appearance is observed when comparing to finished products made with other substrate based pigments.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding U.S. provisional application No. 62/473,581, filed Mar. 20, 2017, are incorporated by reference herein.

The invention claimed is:

1. A pigment powder consisting of coated BiOCl flakes, which flakes are selected from the group consisting of
    a) BiOCl flakes having a coating consisting of yellow iron oxide $Fe_2O_3 \cdot xH_2O$, and optionally a colorant, a surfactant, nano-particles of a metal or metal oxide or metal salt, or $SiO_2$,
    b) BiOCl flakes having a coating consisting of
        $SiO_2$, and
        optionally a colorant, a surfactant or nano-particles of a metal or metal oxide or metal salt,
        wherein the coated BiOCl flakes consist of 90-95% by weight of BiOCl flakes and 5-10% by weight of the coating, where the % by weight are based on the total weight of the coated BiOCl flakes,
    c) BiOCl flakes having a coating consisting of
        a colorant,
        $SiO_2$, and
        optionally yellow iron oxide $Fe_2O_3 \cdot xH_2O$, a surfactant, or nano-particles of a metal or metal oxide or metal salt,
        and
    d) BiOCl flakes having a coating consisting of
        $Fe_3O_4$, and
        optionally $SiO_2$,
        wherein the coated BiOCl flakes consist of 75-95% by weight of BiOCl flakes, 5-20% by weight of $Fe_3O_4$, and 0-5% by weight of $SiO_2$, where the % by weight are based on the total weight of the coated BiOCl flakes;
    and
    wherein, in a), b), c) and d),
    the BiOCl flakes without counting the coating have a thickness of <100 nm, the coatings are directly on the BiOCl flakes, and the coated BiOCl flakes optionally contain an organic after coating.

2. The pigment powder according to claim 1, wherein the coated BiOCl flakes are selected from the group consisting of
    a) coated BiOCl flakes, wherein the coating consist of a first layer and optionally a second layer, wherein the first layer consists of yellow iron oxide $Fe_2O_3 \cdot xH_2O$, and optionally a colorant, a surfactant or nano-particles of a metal or metal oxide or metal salt, and the optional second layer consists of $SiO_2$,
    b) coated BiOCl flakes having a layer consisting of $SiO_2$, wherein the coated BiOCl flakes consist of 90-95% by weight of BiOCl flakes and 5-10% by weight of the $SiO_2$, where the % by weight are based on the total weight of the coated BiOCl flakes,
    c) coated BiOCl flakes, wherein the coating consist of a first layer and optionally a second layer, wherein the first layer consists of a colorant, $SiO_2$, and optionally yellow iron oxide $Fe_2O_3 \cdot xH_2O$, is a surfactant or nano-particles of a metal or metal oxide or metal salt, and the optional second layer consists of $SiO_2$, and
    d) coated BiOCl flakes, wherein the coating consist of a first layer and optionally a second layer, wherein the first layer consists of $Fe_3O_4$ and the optional second layer consists of $SiO_2$, wherein the coated BiOCl flakes consist of 75-95% by weight of BiOCl flakes, 5-20% by weight of $Fe_3O_4$, and 0-5% by weight of $SiO_2$, where the % by weight are based on the total weight of the coated BiOCl flakes.

3. The pigment powder according to claim 1, wherein the coated BiOCl flakes contain an organic after coating.

4. The pigment powder according claim 1, wherein the coated BiOCl flakes consist of 70-92% by weight of BiOCl flakes and 8-30% by weight of yellow iron oxide $Fe_2O_3 \cdot xH_2O$, where the % by weight are based on the total weight of the coated BiOCl flakes.

5. The pigment powder according to claim 1, wherein the coated BiOCl flakes consist of 55-94.99% by weight of BiOCl flakes, 5-40% by weight of yellow iron oxide $Fe_2O_3 \cdot xH_2O$, and 0.01-5% by weight of $SiO_2$, where the % by weight are based on the total weight of the coated BiOCl flakes.

6. The pigment powder according to claim 1, wherein the coated BiOCl flakes consist of 57 to 89.98% by weight of BiOCl flakes, 0.01-3% by weight of yellow iron oxide $Fe_2O_3 \cdot xH_2O$, 5 to 20% by weight of a colorant, 5-15% by weight of $SiO_2$, and 0.01-5% by weight of a surfactant or nano-particles of a metal or metal oxide or metal salt, where the % by weight are based on the total weight of the coated BiOCl flakes.

7. The pigment powder according to claim 1, wherein the coated BiOCl flakes consist of 94-95% by weight of BiOCl flakes and 5-6% by weight of $SiO_2$, where the % by weight are based on the total weight of the coated BiOCl flakes.

8. The pigment powder according to claim 1, wherein the coated BiOCl flakes consist of 75-95% by weight of BiOCl flakes, 5-20% by weight of $Fe_3O_4$, and 3-5% by weight of $SiO_2$, where the % by weight are based on the total weight of the coated BiOCl flakes.

9. The pigment powder according to claim 1, wherein the colorant is an FD&C colorant or an D&C colorant or the lake form of a colorant, or phthalocyanine blue or green.

10. The pigment powder according to claim 1, wherein BiOCl flakes have a particle size<25 µm.

11. A process for the production of the pigment powder according to claim 1, comprising coating uncoated BiOCl flakes by a wet-chemical method and the resultant coated BiOCl flakes are worked up, subsequently spray-dried or oven dried, and optionally baked at 200 to 400° C. under an inert atmosphere.

12. A composition, comprising a pigment powder according to claim 1.

13. The composition according to claim 12, additionally comprising at least one constituent selected from the group consisting of absorbents, astringents, antimicrobial substances, antioxidants, antiperspirants, antifoaming agents, antidandruff active ingredients, antistatics, binders, biological additives, bleaching agents, chelating agents, deodorants, emollients, emulsifiers, emulsion stabilisers, dyes, humectants, film formers, fillers, odour substances, flavour substances, insect repellents, preservatives, anticorrosion agents, cosmetic oils, solvents, oxidants, vegetable constituents, buffer substances, reducing agents, surfactants, propellant gases, opacifiers, UV filters, UV absorbers, denaturing agents, viscosity regulators, perfume and vitamins.

14. A product selected from the group consisting of cosmetics, paints, coatings, inks, plastics, and films, comprising a pigment powder according to claim 1.

15. The pigment powder according to claim 1, which is a dry liquid free powder.

16. The pigment powder according to claim 1, wherein, in the yellow iron oxide $Fe_2O_3*xH_2O$, x is 0.5 to 1.0.

17. The pigment powder according to claim 1, which is
a) BiOCl flakes having a coating consisting of yellow iron oxide $Fe_2O_3*xH_2O$, and optionally a colorant, a surfactant, nano-particles of a metal or metal oxide or metal salt, or $SiO_2$.

18. The pigment powder according to claim 1, which is
b) BiOCl flakes having a coating consisting of $SiO_2$, optionally a colorant, a surfactant or nano-particles of a metal or metal oxide or metal salt, wherein the coated BiOCl flakes consist of 90-95% by weight of BiOCl flakes and 5-10% by weight of the coating, where the % by weight are based on the total weight of the coated BiOCl flakes, or
c) BiOCl flakes having a coating consisting of a colorant, $SiO_2$, optionally yellow iron oxide $Fe_2O_3*xH_2O$, a surfactant or nano-particles of a metal or metal oxide or metal salt.

19. The pigment powder according to claim 1, which is
d) BiOCl flakes having a coating consisting of $Fe_3O_4$ and optionally $SiO_2$, wherein the coated BiOCl flakes consist of 75-95% by weight of BiOCl flakes, 5-20% by weight of $Fe_3O_4$, and 0-5% by weight of $SiO_2$, where the % by weight are based on the total weight of the coated BiOCl flakes.

* * * * *